United States Patent [19]

Caron et al.

[11] Patent Number: 5,629,331
[45] Date of Patent: May 13, 1997

[54] PROCESS FOR THE PREPARATION OF A TETRAZOLE DERIVATIVE IN TWO CRYSTALLINE FORMS AND NOVEL THE CRYSTALLINE FORMS THEREOF

[75] Inventors: Antoine Caron, Montbazin; Dominique Chantreux; Colette Bouloumie, both of Montpellier, all of France

[73] Assignee: Sanofi, Paris, France

[21] Appl. No.: 544,027

[22] Filed: Oct. 17, 1995

[30] Foreign Application Priority Data

Oct. 19, 1994 [FR] France .................. 94 12459

[51] Int. Cl.$^6$ ..................... A61K 31/415; C07D 403/10
[52] U.S. Cl. .................. 514/381; 548/253; 548/300.7
[58] Field of Search ................ 548/253; 514/381

[56] References Cited

FOREIGN PATENT DOCUMENTS 0420237  4/1991  European Pat. Off. .
0475898  3/1992  European Pat. Off. .

*Primary Examiner*—David B. Springer
*Attorney, Agent, or Firm*—Bacon & Thomas

[57] ABSTRACT

The present invention relates to a process for the preparation of the 2-n.butyl-3-[[2'-(tetrazol-5-yl)biphenyl-4-yl]methyl]-1,3-diazaspiro [4.4]-non-1-en-4-one by reaction of the corresponding nitrile with an alkaline azide and triethylamine hydrochloride, recovering the 2-n.butyl-3-[[2'-(tetrazol-5-yl)biphenyl-4-yl]methyl]-1,3-diazaspiro[4.4]non-1-en-4-one in form of one of its alkaline salts in aqueous solution, by neutralization of said alkaline salt and crystallization of the 2-n.butyl-3-[[2'-(tetrazol-5-yl)-biphenyl-4-yl]methyl]-1,3-diazaspiro[4.4]non-1-en-4-one thus precipitated either in a solvent containing less than 10% of water or in a solvent containing more than 10% of water in order to obtain two differents crystalline forms. Furthermore a novel crystalline form of 2-n.butyl-3-[[2'-(tetrazol-5-yl)biphenyl-4-yl]methyl]-1,3-diazaspiro[4.4] non-1-en-4-one and pharmaceutical compositions containing it are described.

13 Claims, 5 Drawing Sheets

PROCESS FOR THE PREPARATION OF A TETRAZOLE DERIVATIVE IN TWO CRYSTALLINE FORMS AND NOVEL THE CRYSTALLINE FORMS THEREOF

FIELD OF THE INVENTION

The present invention concerns a process for the preparation of the 2-n.butyl-4-spirocyclopentane-1-[[2'-(tetrazol-5-yl)biphenyl-4-yl]methyl]-2-imidazolin-5-one in two different crystalline forms, a novel crystalline form of this product and pharmaceutical compositions containing said novel crystalline form. More particularly, the invention relates to the preparation of the 2-n.butyl-4-spirocyclopentane-1-[[2'-(tetrazol-5-yl)-biphenyl-4-yl]methyl]-2-imidazolin-5-one by reaction of the corresponding nitrile with an alkaline azide and triethylamine hydrochloride and to the isolation of said 2-n.butyl-4-spirocyclopentane-1-[[2'-(tetrazol-5-yl)biphenyl-4-yl]methyl]-2-imidazolin-5-one in two different crystalline forms.

BACKGROUND OF THE INVENTION

The 2-n.butyl-4-spirocyclopentane-1-[[2'-(tetrazol-5-yl)-biphenyl-4-yl]methyl]-2-imidazolin-5-one, or 2-n.butyl-3-[[2'-(tetrazol-5-yl)biphenyl-4-yl]methyl]-1,3-diazaspiro[4.4]non-1-en-4-one, is a powerful angiotensin II receptor antagonist prepared by reaction of 2-n.butyl-1-[(2'-cyanobiphenyl-4-yl)methyl]-4-spirocyclopentane-2-imidazolin-5-one, or 2-n.butyl-3-[(2'-cyanobiphenyl-4-yl) methyl]-1,3-diazaspiro-[4.4]non-1-en-4-one, either with tributyltin azide and triphenylchloromethane in xylene at reflux, by elimination of the triphenylmethyl protecting group and by isolation from a solution in ethyl acetate, duly dried (EP-A-0 454 511), or directly with tributyltin azide, in xylene at reflux and isolation from a solution in dichloromethane, duly dried (C. A. Bernhart et al., J. Med. Chem., 1993, 36, 3371–3380). The compound thus prepared, to which the formula (A)

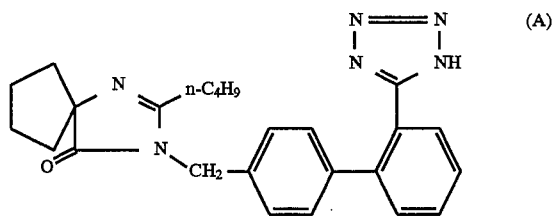

has been attributed, is presented in the form of stable, non-hygroscopic needles which can be stored and formulated without any degradation. However, it has been observed that the 2-n.butyl-3-[[2'-(tetrazol-5-yl)biphenyl-4-yl]methyl]-1,3-diazaspiro[4.4]non-1-en-4-one obtained according to the above described processes, must be formulated with much care because the powder tends to remain attached to the apparatus, for example to the sieves, to the punches or to the mixer walls, due to its high electrostaticity.

DESCRIPTION OF THF PRIOR ART

It is known that another non-peptide angiotensin II antagonist, losartan, namely the potassium salt of the 2-n.butyl-4-chloro-5-hydroxymethyl-1-[2'-(tetrazol-5-yl)biphenyl-4-yl]imidazole exists in two polymorphic forms: one (form I) being regularly obtained at the end of the process of preparation and the other one (form II) being obtained by heating form I at 250° C. Form I of losartan is stable at room temperature whereas form II is stable at high temperature. Consequently, form II is gradually converted to form I which is thermodynamically more stable at room temperature (K. Raghavan et al., Pharm. Res., 1993, 10, 900–904; L. S. Wu et al., Pharm. Res., 1993, 10, 1793–1795).

The transformation of nitriles into tetrazoles by reaction with sodium azide and triethylamine hydrochloride is described in the literature.

Thus, for example, in an article of P. R. Bernstein and E. P. Vacek, Synthesis, 1987, 1133–1134, the different methods of transformation of nitriles into tetrazoles are reviewed and improved conditions for said transformation are proposed. More particularly, in this article it is indicated that when the reaction of sodium azide with triethylamine hydrochloride is carried out in dimethylformamide, a "significant" product formation together with both starting and decomposition products is observed. The improved conditions proposed by the authors consist of the use of 1-methylpyrrolidin-2-one as a solvent at a temperature of about 150° C., namely at a temperature at which a reflux is observed. Under these conditions, the yields are very variable depending on the products (from 60 to 98% before and from 43 to 76% after crystallization).

When preparing the 5-{4-[2-(benzyloxycarboxamino) ethyl]-phenoxymethyl}-(1H)-tetrazole, described in DE 3829431, the starting nitrile is treated with sodium azide and triethylamine hydrochloride in 1-methylpyrrolidine-2-one at a temperature of 150° C. during 8 hours.

Document GB 2184121 describes five preparations of leukotriene antagonist tetrazoles starting from the corresponding nitriles by reaction with sodium azide and triethylamine hydrochloride in dimethylformamide at a temperature of 130°–135° C. to 160° C. The final product yields of said preparations are not given, but P. R. Bernstein and E. P. Vacek, in the above-cited article, have demonstrated that the tetrazole yields are low when operating in dimethylformamide.

According to all the teachings all the above documents, as well as according to the teachings of C. A. Bernhart et al. and EP 0 454 511, cited above, the final product is isolated by evaporation of the solvent and optional crystallization.

SUMMARY OF THE INVENTION

It has now been found that, if the 2-n.butyl-3-[[2'-(tetrazol-5-yl)biphenyl-4-yl]methyl]-1,3-diazaspiro[4.4] non-1-en-4-one is crystallized from a solvent which is more or less poor in water, either the 2-n.butyl-3-[[2'-(tetrazol-5-yl)biphenyl-4-yl]methyl]-1,3-diazaspiro[4.4]non-1-en-4-one is obtained in the crystalline form corresponding to that of the product obtained according to C. A. Bernhart et al. or according to EP-A-0 454 511 cited above, hereinbelow referred to as "Form A", or the 2-n.butyl-3-[[2'-(tetrazol-5-yl)biphenyl-4-yl]methyl]-1,3-diazaspiro[4.4]-non-1-en-4-one is obtained in a novel crystalline form which is very stable and which has a well defined structure, hereinbelow referred to as "Form B". More particularly, it has been found that the novel crystalline form of the 2-n.butyl-3-[[2'-(tetrazol-5-yl)biphenyl-4-yl]methyl]-1,3-diazaspiro[4.4]-non-1-en-4-one (Form B) is at least as stable as the Form A described in EP-A-0 454 511 and J. Med. Chem., 1993, 36, 3371–3380, and that it is not spontaneously converted to the previously known Form A and that, in addition, it is much less electrostatic than Form A; hence it can be more easily subjected to any treatment under the usual conditions of pharmaceutical techniques. By the X-ray diffractometric analysis of the monocrystal solid, it has been observed, unexpectedly, that the novel crystalline form of 2-n.butyl-3-[[2'(tetrazol-5-yl)biphenyl-4-yl]methyl]-1,3-diazaspiro[4.4]non-1-en-4-one is constituted by triclinic cristals of the pure tautomer having the hydrogen atom of the tetrazole ring in the 2-position, represented by the formula (B)

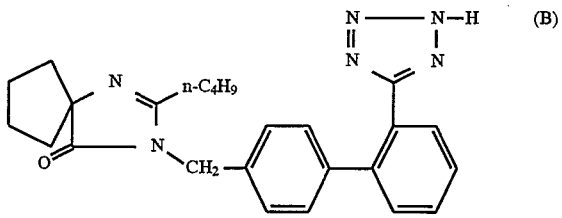

Finally, it has been found that 2-n.butyl-3-[[2'-(tetrazol-5-yl)biphenyl-4-yl]methyl]-1,3-diazaspiro[4.4]non-1-en-4-one can be obtained with excellent yields without using tin derivatives by reaction of the 2-n.butyl-3-[(2'-cyanobiphenyl-4-yl]methyl-1,3-diazaspiro[4.4]non-1-en-4-one with an alkaline azide and triethylamine hydrochloride in an inert polar aprotic solvent and by neutralization in an aqueous medium of one of its alkaline salts, by isolating it either in its Form A or in its Form B. More particularly, the Form A or Form B yields, which are pure at at least 99,8%, are of 80% or more.

BRIEF DESCRIPTION OF THE DRAWINGS

The difference between the novel crystalline form of the 2-n.butyl-3-[[2'(tetrazol-5-yl)biphenyl-4-yl]methyl]-1,3-diazaspiro[4.4]-non-1-en-4-one according to the present invention (Form B) and the Form A described by the above-cited C. A. Bernhart et al. emerges from the examination of FIGS. 1 and 2, while

FIG. 3 gives the developed formula of the 2-n.butyl-3-[[2'-(tetrazol-5-yl)biphenyl-4-yl]methyl]-1,3-diazaspiro[4.4]non-1-en-4-one, with the numbering of the atoms, when it is present in crystalline form B;

FIG. 4 gives the spatial configuration of the 2-n.butyl-3-[[2'-(tetrazol-5-yl)biphenyl-4-yl]methyl]-1,3-diazaspiro[4.4]non-1-en-4-one molecule, Form B, in the crystal;

FIG. 5 shows the cyclic dimer of the 2-n.butyl-3-[[2'-(tetrazol-5-yl)biphenyl-4-yl]methyl]-1,3-diazaspiro[4.4]non-1-en-4-one in the triclinic crystals of Form B, formed by the hydrogen bonds N(25)-H . . . N(3); two molecules of 2-n.butyl-3-[[2'-(tetrazol-5-yl)biphenyl-4-yl]methyl]-1,3-diazaspiro[4.4]non-1-en-4-one are disposed in the crystals of Form B to form "dimers" (although it is improper because the two molecules are not linked by covalent bonds the term dimer is used since these two molecules are assembled by hydrogen bonds, between the hydrogen atom in the 2-position of the tetrazole and the nitrogen atom in the 3-position of the imidazolinone ring, which stabilize the (2H)-5-tetrazolyl structure).

Figure 1:
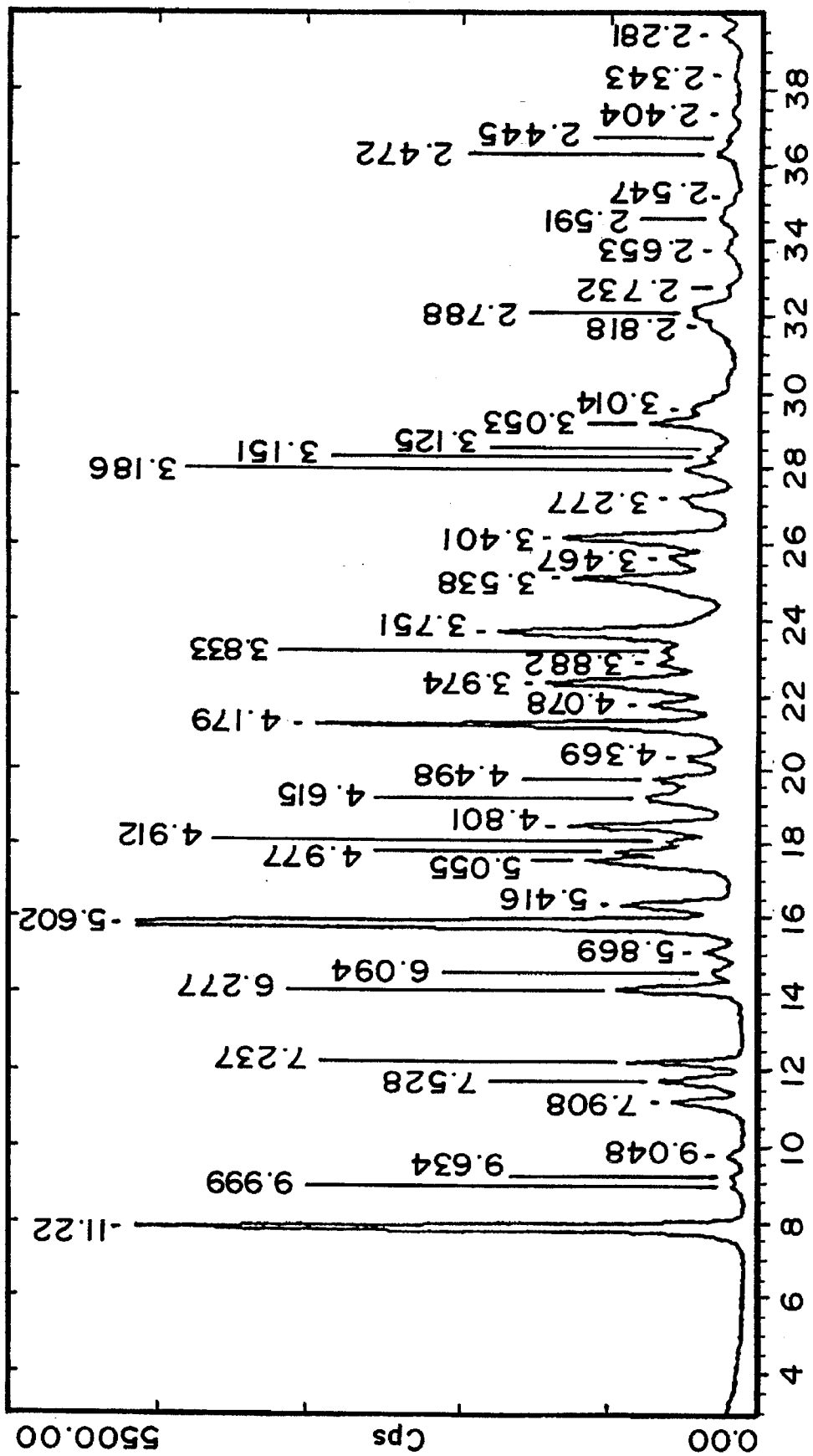
FIG. 1 gives the X-ray powder diffraction spectrum of the 2-n.butyl-3-[[2'-(tetrazol-5-yl)biphenyl-4-yl]methyl]-1,3-diazaspiro[4.4]non-1-en-4-one, Form B, showing the maximal intensity at the interreticular spacing of 11.22Å and high intensities at 5.60 and 4.17Å.

Thus, according to one of its aspects, the present invention relates to a process for the preparation of the 2-n.butyl-3-[[2'-(tetrazol-5-yl)biphenyl-4-yl]methyl]-1,3-diazaspiro [4.4]non-1-en-4-one which comprises the steps of:

(a) treating the 2-n.butyl-3-[(2'-cyanobiphenyl-4-yl) methyl]-1,3-diazaspiro-[4.4]-non-1-en-4-one with an alkaline azide and triethylamine hydrochloride in an inert polar aprotic solvent and then recovering the thus obtained 2-n.butyl-3-[[2'-(tetrazol-5-yl)biphenyl-4-yl] methyl]-1,3-diazaspiro[4.4]non-1-en-4-one in the form of one of its alkaline salts in aqueous solution;

(b) neutralizing the alkaline salt of the thus obtained 2-n.butyl-3-[[2'-(tetrazol-5-yl) biphenyl-4-yl]methyl]-1,3-diazaspiro[4.4]non-1-en-4one in aqueous medium until the pH is of from 4.7 to 5.3; and (c) crystallizing the thus precipitated product:
either in a solvent containing less than about 10% in volume of water to isolate the 2-n.butyl-3-[[2'-(tetrazol-5-yl)biphenyl-4-yl]methyl]-1,3-diazaspiro [4.4]non-1-en-4-one in its Form A;
or in a water-miscible solvent containing more than about 10% in volume of water to isolate the 2-n.butyl-3-[[2'-(tetrazol-5-yl)biphenyl-4-yl]methyl] -1,3-diazaspiro[4.4]non-1-en-4-one in its Form B.

More particularly, in step (a), the starting 2-n.butyl-3-[(2'-cyanobiphenyl-4-yl)methyl]-1,3-diazaspiro[4.4]non-1-en-4-one is mixed with the alkaline azide, preferably sodium azide and triethylamine hydrochloride in an inert aprotic polar solvent such as N,N-dimethylformamide, N,N-dimethylacetamide, dimethyl sulfoxide, 1-methylpyrrolidin-2-one. Among the aprotic polar solvents used in this step, dimethylformamide and 1-methylpyrrolidin-2-one are particularly advantageous.

Although the reaction can be carried out at reflux, it has been observed that the use of lower temperatures is very advantageous for making the process economical to use because it prevents azide compounds from being carried with the refrigerants during reflux, which would involve safety risks.

Preferably, the reaction mixture is heated at a temperature lower than the reflux temperature, advantageously 10°–30° C. lower, more particularly at a temperature of 110° to 140° C. when dimethylformamide or 1-methylpyrrolidin-2-one is used as a solvent. In dimethylformamide the reaction is generally carried out at 115°–125° C.; in 1-methylpyrrolidin-2-one the optimum reaction temperature is 120°–130° C., even if it is possible to reach 140° C.

According to the present invention, equimolecular amounts of sodium azide and triethylamine hydrochloride are used, in proportions of 1.5 to 5 moles per mole of starting nitrile, advantageously from about 2 to about 4 moles per mole of nitrile. Under these conditions, it is possible to operate in a concentrated medium, and even highly concentrated, using 0.6 to 7 liters of solvent, per mole of starting nitrile.

After 6–20 hours of heating, the reaction is over and the reaction mixture is treated according to the conventional techniques. More particularly, the mixture is neutralized by addition of a base, for example an alkaline hydroxide, in aqueous solution, the aqueous phase containing the salts, particularly chlorides and azides; is removed. The organic phase is thus treated with water and organic solvents such as toluene, ethyl acetate, or even two different solvents successively if necessary, in order to eliminate the reaction by-products.

The thus isolated aqueous phase, containing the alkaline salt of the 2-n.butyl-3-[[2'-(tetrazol-5-yl)biphenyl-4-yl]

methyl]-1,3-diazaspiro-[4.4]non-1-en-4-one, is subjected to step (b) consisting of an acidification, preferably by addition of hydrochloric acid until the pH is of from 4.7 to 5.3, preferably between 4.8 and 5.2 in order to obtain a crude 2-n.butyl-3-[[2'-(tetrazol-5-yl)biphenyl-4-yl]methyl]-1,3-diazaspiro[4.4]non-1-en-4-one already having a satisfactory degree of purity after having well eliminated the solvent from the product.

The global yield when starting from nitrile is very high (up to 80–90% of the theory).

In step (c), the thus obtained product is subjected to a crystallization in order to obtain the 2-n.butyl-3-[[2'-(tetrazol-5-yl)biphenyl-4-yl]methyl]-1,3-diazaspiro[4.4]non-1-en-4-one either in its Form A or in its Form B.

To obtain Form A, the resulting product is crystallized from a solvent containing less than about 10% in volume of water, preferably from an anhydrous solvent, the presence of such amounts of water not being critical. The preferred solvents are the alcohols, particularly 95% ethanol or isopropanol, the crystallization conditions being those usually employed in this type of operation.

To obtain Form B, the product obtained at the end of step (b) is crystallized under stirring in a water-miscible solvent containing an amount of water greater than about 10%. For this crystallization the presence of water is critical. The water-miscible organic solvents which may be used are for example alcohols, particularly methanol, ethanol and isopropanol, ketones, particularly acetone, ethers such as tetrahydrofurane or dioxane, nitriles, particularly acetonitrile. Also to obtain Form B, the technique is that usually employed in crystallization operations.

The formation of Forms A and B is relatively independent of the cooling rate and seeding can be useful, but it is not essential.

The percent in volume of water in the organic solvent has been fixed at about 10% as a maximal and minimal amount respectively for the preparation of Form A and Form B, but this percent represents a limit value which also depends on the organic solvent used. For example, an amount of 9–11% of water is sufficient to obtain 100% of Form B when an acetone/water mixture is used for the preparation of Form B. However, it is advantageous to use a percent in volume of at least 15% of water for the preparation of Form B, preferably of 15 to 50%. In the same way, when for example isopropanol is used for the preparation of Form A, said Form A is obtained even when the organic solvent contains 9–11% of water. More particularly, it is preferable to use an anhydrous solvent, although 100% of Form A is obtained in 95 ethanol.

The fact that the presence of water and its absence are critical makes it possible to pass from a crystalline form to the other by a recrystallization under the above conditions. In fact, it was observed that Form A can be converted to Form B by recrystallization, for example from a hydroalcoholic solution, whereas a recrystallization, for example, from isopropanol, gives Form A again, even after seeding with Form B. Similarly, Form B is converted to Form A by recrystallization from isopropanol.

Such an observation made it possible to develop a process for the preparation of the Form B of the 2-n.butyl-3-[[2'-(tetrazol-5-yl)biphenyl-4-yl]methyl]-1,3-diazaspiro[4.4]non-1-en-4-one starting from the Form A obtained by the known processes, described for example in the C. A. Bernhart et al. article and in EP-A-0 454 511 or starting from the alkaline salts of the 2-n.butyl-3-[[2'-(tetrazol-5-yl)biphenyl-4-yl]methyl]1,3-diazaspiro[4.4]non-1-en-4-one, especially from the potassium salt.

Thus, according to another of its aspects, the present invention relates to a process for the preparation of the Form B of the 2-n.butyl-3-[[2'-(tetrazol-5-yl)biphenyl-4-yl]methyl]-1,3-diazaspiro[4.4]non-1-en-4-one which comprises recrystallizing a 2-n.butyl-3-[[2'-(tetrazol-5-yl)biphenyl-4-yl]-methyl]-1,3-diazaspiro[4.4]non-1-en-4-one as a raw material or in its Form A from a water-miscible solvent containing at least about 10% of water.

More particularly, when the starting 2-n.butyl-3-[[2'-(tetrazol-5-yl)biphenyl-4-yl]methyl]-1,3-diazaspiro[4.4]non-1-en-4-one is in the form of a raw product, crystallization is generally carried out under the conditions set forth above, namely by using a solvent such as an alcohol, acetone, tetrahydrofurane or acetonitrile in the presence of at least 10% of water, advantageously of at least 15%, preferably 15–50% of water. The 2-n.butyl-3-[[2'-(tetrazol-5-yl)biphenyl-4-yl]methyl]-1,3-diazaspiro[4.4]-non-1-en-4-one as a raw product used as the starting compound may be that obtained from an alkaline salt of the 2-n.butyl-3-[[2'-(tetrazol-5yl)biphenyl-4-yl]methyl]-1,3-diazaspiro[4.4]-non-1-en-4-one after dissolution in water, neutralization with an acid until the pH is of from 4.7 to 5.3 and filtration of the precipitate. This procedure is suggested when the 2-n.butyl-3-[[2'-(tetrazol-5-yl)biphenyl-4-yl]methyl]-1,3-diazaspiro[4.4]-non-1-en-4-one is stored in the form an alkaline salt, preferably a potassium salt.

When the starting 2-n.butyl-3-[[2'-(tetrazol-5-yl) biphenyl-4-yl]methyl]-1,3-diazaspiro[4.4]non-1-en-4-one is in its Form A, the crystallization conditions are very flexible because the amount of water which is present, always at least 10%, may vary from 10% to 100%. This is due to the fact that the starting Form A is already very pure and, hence, the organic solvent is no longer necessary. Nevertheless, it is to be considered that, when operating in water only, transformation is very slow and it must be accelerated by adding an acid such as hydrochloric acid until the pH is 2–3, namely without causing the formation of the acid addition salt such as the hydrochloride.

The novel Form B is isolated by simple filtration and desiccation.

Although the presence of water is critical for the formation of the Form B of the 2-n.butyl-3-[[2'-(tetrazol-5-yl) biphenyl-4-yl]methyl]-1,3-diazaspiro[4.4]non-1-en-4-one, no transformation of Form A into Form B is observed under the normal conditions of pharmaceutical formulation. More particularly, for example, no formation of Form B is observed during the wet granulation of Form A.

Thus, according to another of its aspects, the present invention provides the Form B of the 2-n.butyl-3-[[2'-(tetrazol-5-yl)biphenyl-4-yl]methyl]-1,3-diazaspiro[4.4] non-1-en-4-one, characterized by the X-ray powder diffraction pattern illustrated in Table I.

More particularly, the Form B of the 2-n.butyl-3-[[2'-(tetrazol-5-yl)biphenyl-4-yl]methyl]-1,3-diazaspiro[4.4] non-1-en-4-one is also characterized by a melting point of 185°–186° C., determined by differential scanning calorimetry (DSC) and by characteristic infrared absorbances at 1537, 1200 and 745 $cm^{-1}$.

The physical properties and the behaviour of the novel crystalline form (Form B) of the 2-n.butyl-3-[[2'-(tetrazol-5-yl)biphenyl-4-yl]methyl]1,3-diazaspiro[4.4]non-1-en-4-one according to the present invention are completely different from those of Form A described by C. A. Bernhart et al. and by EP 0 454 511 cited above, as was demonstrated by examining the two forms, according to the conventional methods and techniques.

Figure 2:
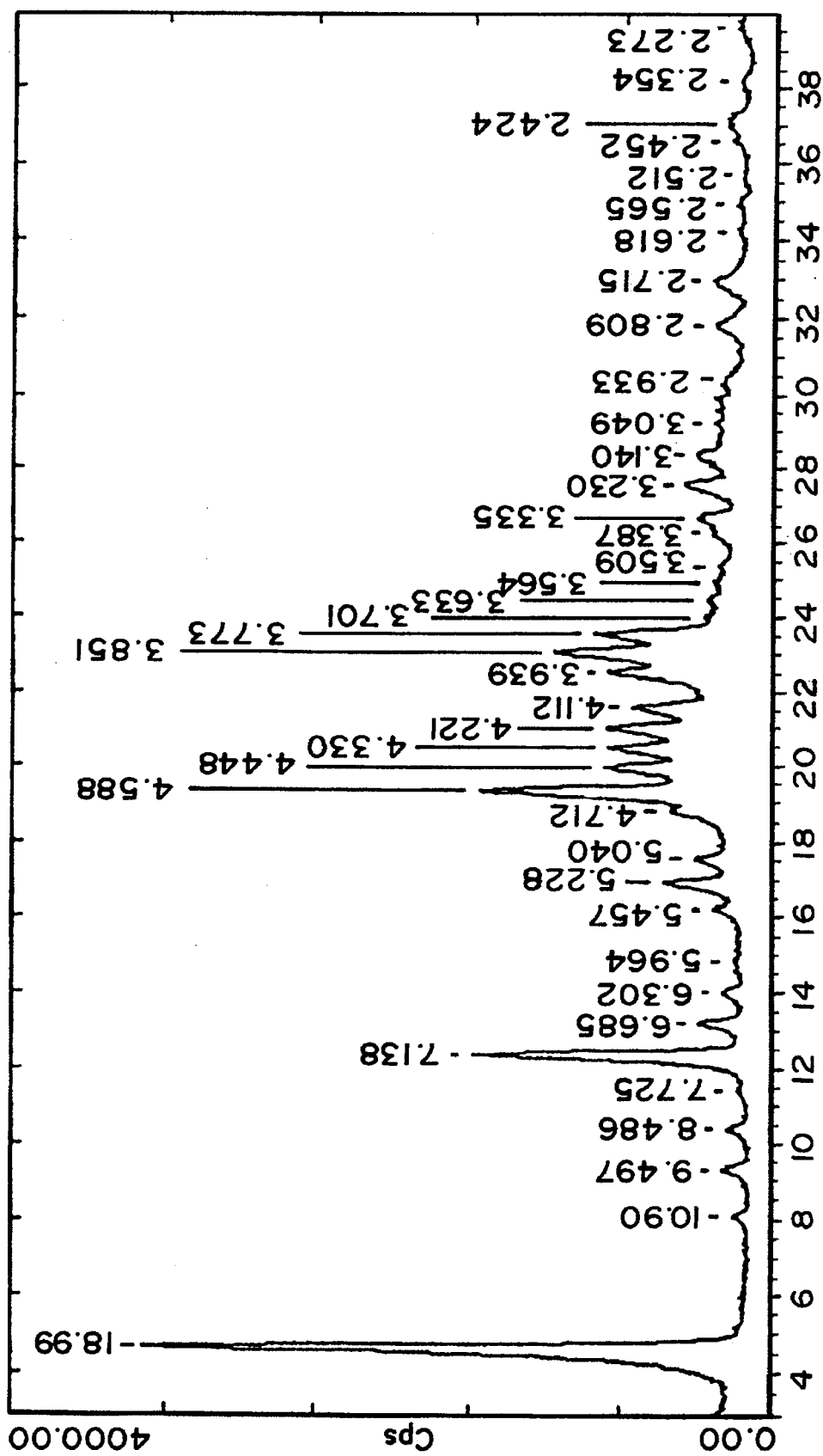
FIG. 2 gives the X-ray powder diffraction spectrum of the 2-n.butyl-3-[[2'-(tetrazol-5-yl)biphenyl-4-yl]methyl]-1,3-diazaspiro[4.4]non-1-en-4-one, Form A, showing the maximal intensity at the interreticular spacing of 18.99Å and relatively high intensities at 7.13 and 4.58Å.

The X-ray powder diffraction pattern (angle of diffraction) was established with a Siemens D500TT diffractometer. The characterictic spectra in the range of 5° to 40° (2-theta) are shown in FIG. 1 for the Form B and in FIG. 2 for the Form A. The significant lines of FIG. 1 are listed in Table I and those of FIG. 2 are collated in Table II.

In Tables I and II, d is the interreticular spacing and $I/I_o$ is the relative intensity, which is expressed in percent of the most intense line.

TABLE I

| d | $I/I_o$ |
|---|---|
| 11.22 | 100.00 |
| 7.90 | 12.02 |
| 7.52 | 13.79 |
| 7.23 | 18.60 |
| 6.27 | 20.14 |
| 6.09 | 6.47 |
| 5.86 | 7.42 |
| 5.60 | 98.76 |
| 5.41 | 19.45 |
| 5.05 | 24.67 |
| 4.97 | 20.36 |
| 4.91 | 12.92 |
| 4.80 | 27.33 |
| 4.61 | 15.90 |
| 4.49 | 14.73 |
| 4.36 | 9.86 |
| 4.17 | 62.84 |
| 4.07 | 15.39 |
| 3.97 | 30.34 |
| 3.88 | 14.32 |
| 3.83 | 13.56 |
| 3.75 | 37.28 |
| 3.53 | 26.48 |
| 3.46 | 12.42 |
| 3.40 | 27.88 |
| 3.27 | 11.03 |
| 3.18 | 10.42 |
| 3.15 | 7.28 |
| 3.12 | 6.11 |
| 3.05 | 15.50 |
| 3.01 | 9.49 |
| 2.81 | 7.11 |
| 2.78 | 9.40 |

TABLE II

| d | $I/I_o$ |
|---|---|
| 18.98 | 100.00 |
| 10.89 | 5.81 |
| 9.49 | 7.43 |
| 8.48 | 6.60 |
| 7.13 | 46.23 |
| 6.68 | 11.25 |
| 6.30 | 7.45 |
| 5.45 | 8.85 |
| 5.22 | 16.82 |
| 5.03 | 11.81 |
| 4.71 | 15.91 |
| 4.58 | 45.40 |
| 4.44 | 26.12 |
| 4.32 | 25.44 |
| 4.22 | 25.86 |
| 4.11 | 21.72 |
| 3.93 | 25.46 |
| 3.85 | 33.89 |
| 3.77 | 27.76 |
| 3.38 | 9.09 |
| 3.33 | 11.75 |
| 3.23 | 13.68 |
| 3.14 | 11.99 |
| 2.80 | 8.97 |
| 2.71 | 9.50 |

The differential scanning calorimetry (DSC) of Forms A and B was carded out comparatively by using a Perkin Elmer DSC7 apparatus, calibrated with reference to indium and cyclohexane.

3 to 6 mg of Form A or 3 to 6 mg of Form B, as obtained in Example 2, in a crimped, pierced aluminium sample holder, within a range of temperature of 20° to 200° C. at the heating rate of 10° C./minute were used for the calorimetric analysis. The melting point and the melting enthalpy are given in Table III. The melting point corresponds to the characteristic melting temperature obtained by DSC. This value may also be defined as the temperature corresponding to the intersection of the baseline and the tangent to the melting peak rising observed by DSC.

TABLE III

| | Form A | Form B |
|---|---|---|
| Melting point (°C.) | 182.8 | 185.6 |
| Melting enthalpy (J/g) | 92.2 | 115.5 |

It results from this table that Form B is thermodynamically more stable than Form A.

The difference between the novel Form B and the known Form A of the 2-n.butyl-3-[[2'-(tetrazol-5-yl)biphenyl-4-yl]methyl]-1,3-diazaspiro[4.4]non-1-en-4-one was also shown by infrared spectroscopy. The Fourier Transformant Infrared (FTIR) spectra from 4000 $cm^{-1}$ to 600 $cm^{-1}$ were obtained with a 4 $cm^{-1}$ resolution Nicolet 5PC spectrometer. The samples were prepared by mixing 2 mg of the Form A or of the Form B with 200 mg of KBr, the whole being then compressed under 2 tons for 2 minutes. Each sample was studied after 32 accumulations.

The comparison of the characteristics lines in terms of wavelength (in $cm^{-1}$) and intensity (in percent of transmittance) is shown in Table IV.

TABLE IV

| | % transmittance | |
|---|---|---|
| Wavelength ($cm^{-1}$) | Form A | Form B |
| 745 | * | 2.5 |
| 758 | 3.7 | * |
| 781 | 17.8 | * |
| 959 | 22.7 | * |
| 1007 | 26.6 | 6.6 |
| 1177 | * | 7.2 |
| 1179 | 23.5 | * |
| 1200 | * | 18.0 |
| 1238 | 26.1 | * |
| 1383 | 20.9 | * |
| 1537 | * | 14.1 |

It results from Table IV that tile Form B presents characteristic absorbances at 745, 1200 and 1537 $cm^{-1}$ which are absent from the Form A.

The particular 2H-tetrazol-5-yl structure of Form B was shown by the X-ray diffraction of a monocrystal by using an MSC-Rigaka AFC6S diffractometer with SHELXS-90 and SHELXS-93 software on a SG IRIS Indigo workstation. The position of the C-H hydrogens was generated at a distance of 0.95 Å.

The crystallographic data, more particularly the interplanar distances (a, b, c), the angles ($\alpha,\beta,\gamma,$) and the volume of each unit cell are shown in Table V

TABLE V

Crystallographic data and structure refinement of Form B
Unit cell dimensions:

| Crystal system | triclinic |
|---|---|
| Space group | P-1 |
| a | 11.170(5)Å |
| b | 12.181(4)Å |
| c | 9.366(4)Å |
| α | 90.75(4) degree |
| β | 105.24(4) degree |
| γ | 112.92(3) degree |
| volume | 1122.9(8)Å$^3$ |

The atomic coordinates of the Form B of the 2-n.butyl-3-[[2'-(tetrazol-5-yl)biphenyl-4-yl]methyl]-1,3-diazaspiro[4.4]non-1-en-4-one are given in Table VI, bond lengths in Table VII, bond angles in Table VIII and characteristic torsion angles in Table IX.

TABLE VI

Positional parameters of Form B

| atom | x | y | z |
|---|---|---|---|
| N(1) | 0.4011(2) | 0.6617(2) | −0.2435(2) |
| C(2) | 0.3178(3) | 0.5684(3) | −0.3565(3) |
| N(3) | 0.3387(2) | 0.5866(2) | −0.4838(3) |
| C(4) | 0.4491(3) | 0.7065(2) | −0.4659(3) |
| C(5) | 0.4859(3) | 0.7514(2) | −0.3022(3) |
| C(6) | 0.4051(4) | 0.7912(4) | −0.5671(4) |
| C(7) | 0.5268(5) | 0.8643(4) | −0.6164(6) |
| C(8) | 0.5872(5) | 0.7781(5) | −0.6362(5) |
| C(9) | 0.5724(3) | 0.7036(3) | −0.5096(4) |
| C(10) | 0.4094(3) | 0.6654(3) | −0.0844(3) |
| C(11) | 0.3135(2) | 0.7106(2) | −0.0433(3) |
| C(12) | 0.2025(3) | 0.6349(2) | −0.0013(3) |
| C(13) | 0.1164(3) | 0.6773(2) | 0.0396(3) |
| C(14) | 0.1380(2) | 0.7977(2) | 0.0394(3) |
| C(15) | 0.2507(3) | 0.8743(2) | −0.0020(3) |
| C(16) | 0.3364(3) | 0.8317(2) | −0.0424(3) |
| C(17) | 0.0528(3) | 0.8477(2) | 0.0923(3) |
| C(18) | −0.0898(3) | 0.7975(2) | 0.0473(3) |
| C(19) | −0.1577(3) | 0.8494(3) | 0.1117(3) |
| C(20) | −0.0879(3) | 0.9494(3) | 0.2184(4) |
| C(21) | 0.0507(3) | 1.0006(3) | 0.2599(4) |
| C(22) | 0.1205(3) | 0.9498(3) | 0.1983(4) |
| C(23) | −0.1774(2) | 0.6935(2) | −0.0688(3) |
| N(24) | −0.1481(2) | 0.6593(2) | −0.1858(2) |
| N(25) | −0.2625(2) | 0.5661(2) | −0.2540(2) |
| N(26) | −0.3573(2) | 0.5423(2) | −0.1882(3) |
| N(27) | −0.3053(2) | 0.6223(2) | −0.0681(3) |
| C(28) | 0.2116(4) | 0.4603(4) | −0.3254(4) |
| C(29) | 0.1072(5) | 0.3772(4) | −0.4633(5) |
| C(30) | −0.0182(4) | 0.2920(5) | −0.4422(5) |
| C(31) | −0.1105(5) | 0.2132(5) | −0.5811(6) |
| O(32) | 0.5713(3) | 0.8456(2) | −0.2336(3) |

TABLE VII

Intramolecular Distances of Form B

| atom | atom | distance |
|---|---|---|
| N(1) | C(5) | 1,370(4) |
| N(1) | C(2) | 1,380(3) |
| N(1) | C(10) | 1.468(3) |
| C(2) | N(3) | 1.279(4) |
| C(2) | C(28) | 1.484(4) |
| N(3) | C(4) | 1.471(4) |
| C(4) | C(5) | 1.513(4) |
| C(4) | C(6) | 1.543(4) |
| C(4) | C(9) | 1.549(4) |
| C(5) | O(32) | 1.202(3) |
| C(6) | C(7) | 1.501(6) |
| C(7) | C(8) | 1.485(7) |
| C(8) | C(9) | 1.507(5) |
| C(10) | C(11) | 1.507(3) |
| C(11) | C(12) | 1,384(4) |
| C(11) | C(16) | 1,396(4) |
| C(12) | C(13) | 1,384(4) |
| C(13) | C(14) | 1,390(4) |
| C(14) | C(15) | 1,399(4) |
| C(14) | C(17) | 1.489(4) |
| C(15) | C(16) | 1,379(4) |
| C(17) | C(22) | 1,395(4) |
| C(17) | C(18) | 1.404(4) |
| C(18) | C(19) | 1,394(4) |
| C(18) | C(23) | 1.477(4) |
| C(19) | C(20) | 1,381(4) |
| C(20) | C(21) | 1,364(5) |
| C(21) | C(22) | 1,389(4) |
| C(23) | N(24) | 1,328(3) |
| C(23) | N(27) | 1,354(3) |
| N(24) | N(25) | 1,324(3) |
| N(25) | N(26) | 1,301(3) |
| N(26) | N(27) | 1,319(3) |
| C(28) | C(29) | 1.519(5) |
| C(29) | C(30) | 1.448(6) |
| C(30) | C(31) | 1.473(6) |

Distances are in Ångstroms. Estimated standard deviations in the last decimal are in brackets.

TABLE VIII

Intramolecular Bond Angles Involving Non-hydrogen Atoms

| atom | atom | atom | angle | atom | atom | atom | angle |
|---|---|---|---|---|---|---|---|
| C(5) | N(1) | C(2) | 108.2(2) | C(13) | C(14) | C(15) | 117.6(2) |
| C(5) | N(1) | C(10) | 123.7(2) | C(13) | C(14) | C(17) | 122.3(2) |
| C(2) | N(1) | C(10) | 127.9(2) | C(15) | C(14) | C(17) | 120.0(2) |
| N(3) | C(2) | N(1) | 114.6(2) | C(16) | C(15) | C(14) | 121.2(2) |
| N(3) | C(2) | C(28) | 125.6(3) | C(15) | C(16) | C(11) | 121.0(2) |
| N(1) | C(2) | C(28) | 119.7(3) | C(22) | C(17) | C(18) | 118.0(2) |
| C(2) | N(3) | C(4) | 107.6(2) | C(22) | C(17) | C(14) | 117.0(2) |
| N(3) | C(4) | C(5) | 103.5(2) | C(18) | C(17) | C(14) | 124.9(2) |

TABLE VIII-continued

Intramolecular Bond Angles Involving Non-hydrogen Atoms

| atom | atom | atom | angle | atom | atom | atom | angle |
|---|---|---|---|---|---|---|---|
| N(3) | C(4) | C(6) | 112.5(3) | C(19) | C(18) | C(17) | 119.2(2) |
| C(5) | C(4) | C(6) | 111.7(3) | C(19) | C(18) | C(23) | 115.6(2) |
| N(3) | C(4) | C(9) | 113.0(2) | C(17) | C(18) | C(23) | 125.1(2) |
| C(5) | C(4) | C(9) | 111.9(2) | C(20) | C(19) | C(18) | 121.6(3) |
| C(6) | C(4) | C(9) | 104.3(3) | C(21) | C(20) | C(19) | 119.6(3) |
| O(32) | C(5) | N(1) | 125.3(3) | C(20) | C(21) | C(22) | 119.9(3) |
| O(32) | C(5) | C(4) | 128.7(3) | C(21) | C(22) | C(17) | 121.7(3) |
| N(1) | C(5) | C(4) | 106.0(2) | N(24) | C(23) | N(27) | 111.5(2) |
| C(7) | C(6) | C(4) | 105.2(3) | N(24) | C(23) | C(18) | 127.3(2) |
| C(8) | C(7) | C(6) | 103.8(3) | N(27) | C(23) | C(18) | 121.2(2) |
| C(7) | C(8) | C(9) | 105.2(3) | N(25) | N(24) | C(23) | 101.8(2) |
| C(8) | C(9) | C(4) | 106.1(3) | N(26) | N(25) | N(24) | 114.4(2) |
| N(1) | C(10) | C(11) | 113.9(2) | N(25) | N(26) | N(27) | 106.2(2) |
| C(12) | C(11) | C(16) | 117.8(2) | N(26) | N(27) | C(23) | 106.1(2) |
| C(12) | C(11) | C(10) | 121.5(2) | C(2) | C(28) | C(29) | 114.7(3) |
| C(16) | C(11) | C(10) | 1120.6(2) | C(30) | C(29) | C(28) | 116.3(4) |
| C(11) | C(12) | C(13) | 121.4(2) | C(29) | C(30) | C(31) | |
| C(12) | C(13) | C(14) | 121.1(2) | | | | |

Angles are in degrees. Estimated standard deviations in the last decimal are given in brackets.

TABLE IX

Characteristic Torsion and Conformation Angles

| (1) | (2) | (3) | (4) | angle |
|---|---|---|---|---|
| N(1) | C(10) | C(11) | C(12) | 110.2(3) |
| N(1) | C(10) | C(11) | C(16) | −71.6(3) |
| N(1) | C(2) | C(28) | C(29) | 167.0(4) |
| N(1) | C(2) | N(3) | C(4) | −0.2(3) |
| C(2) | C(28) | C(29) | C(30) | −162.3(5) |
| C(2) | N(1) | C(10) | C(11) | −89.4(3) |
| C(2) | N(1) | C(5) | C(4) | −0.1(3) |
| C(2) | N(3) | C(4) | C(5) | 0.1(3) |
| N(3) | C(2) | C(28) | C(29) | −10.6(6) |
| N(3) | C(4) | C(5) | N(1) | 0.0(3) |
| C(4) | C(6) | C(7) | C(8) | 36.6(5) |
| C(6) | C(4) | C(9) | C(8) | −3.3(4) |
| C(6) | C(7) | C(8) | C(9) | −38.9(5) |
| C(7) | C(8) | C(9) | C(4) | 25.9(5) |
| C(9) | C(4) | C(6) | C(7) | −20.2(4) |
| C(13) | C(14) | C(17) | C(18) | −49.6(4) |
| C(17) | C(18) | C(23) | N(24) | −28.2(4) |
| C(23) | N(24) | N(25) | N(26) | 0.3(3) |
| N(24) | C(23) | N(27) | N(26) | −0.4(3) |
| N(24) | N(25) | N(26) | N(27) | −0.6(3) |
| N(25) | N(26) | N(27) | C(23) | 40.6(3) |
| C(28) | C(29) | C(30) | C(31) | −178.2(5) |

The sign is positive, if when looking clockwise from atom 2 to atom 3, atom 1 is superimposed on atom 4.

Figure 3:
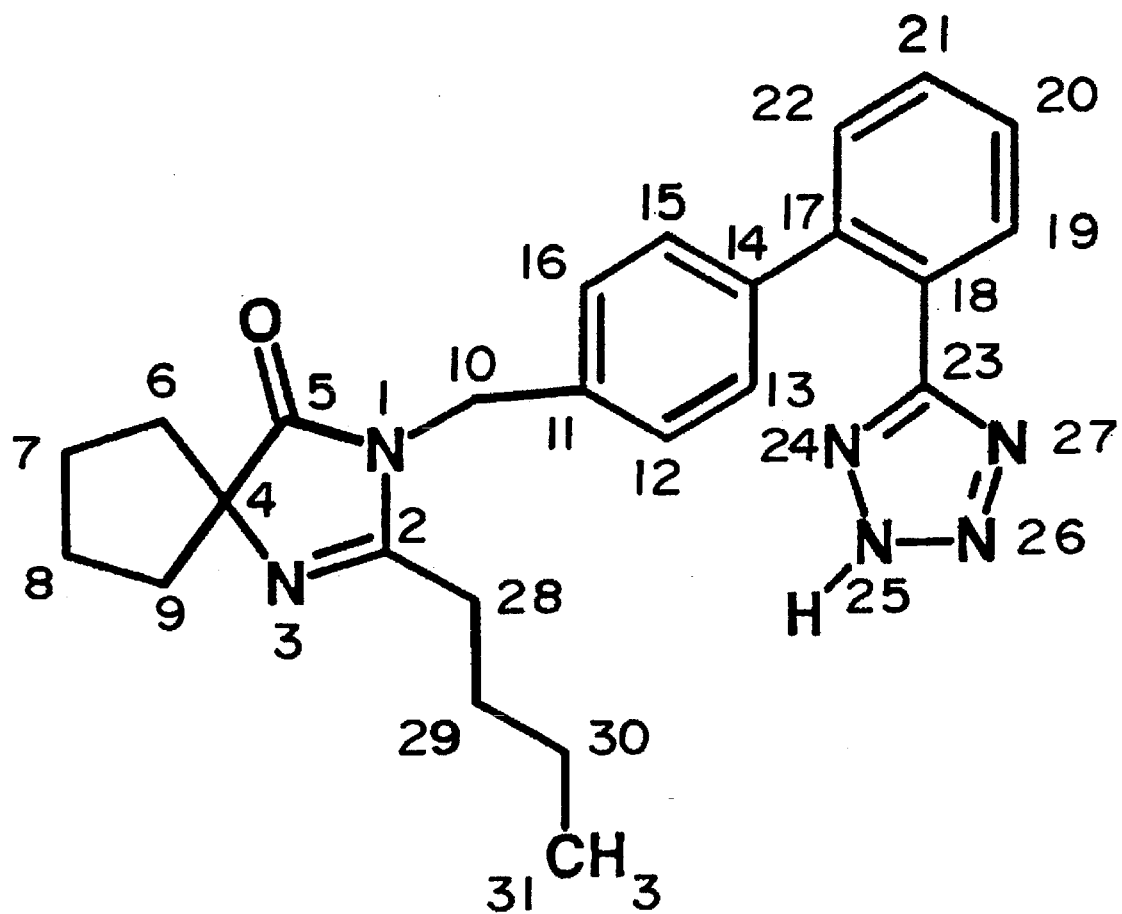
FIGS. 3 to 5 show the structure of the 2-n.butyl-3-[[2'-(tetrazol-5-yl)biphenyl-4-yl]methyl]-1,3-diazaspiro-[4.4]non-1-en-4-one in the crystals of Form B. More particularly.

The X-ray crystallographic study, expecially the crystallographic data of Table I, the atomic coordinates of Table VI, the bond lengths of Table VII, the angles between the bonds of Table VIII and the characteristic torsion angles of Table IX prove the proposed structure (B) as shown in FIG. 3.

Figure 4:
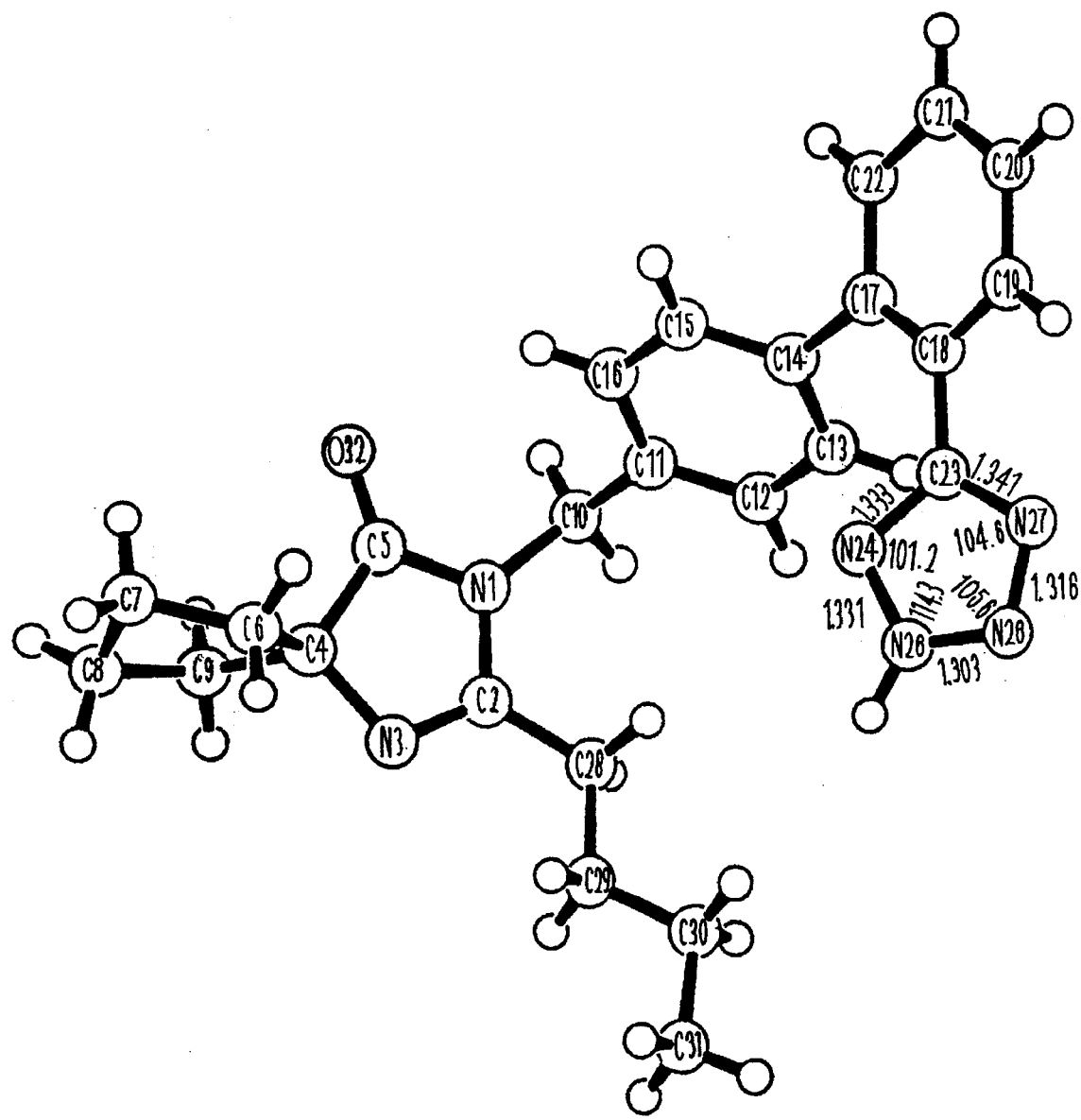
Figure 5:
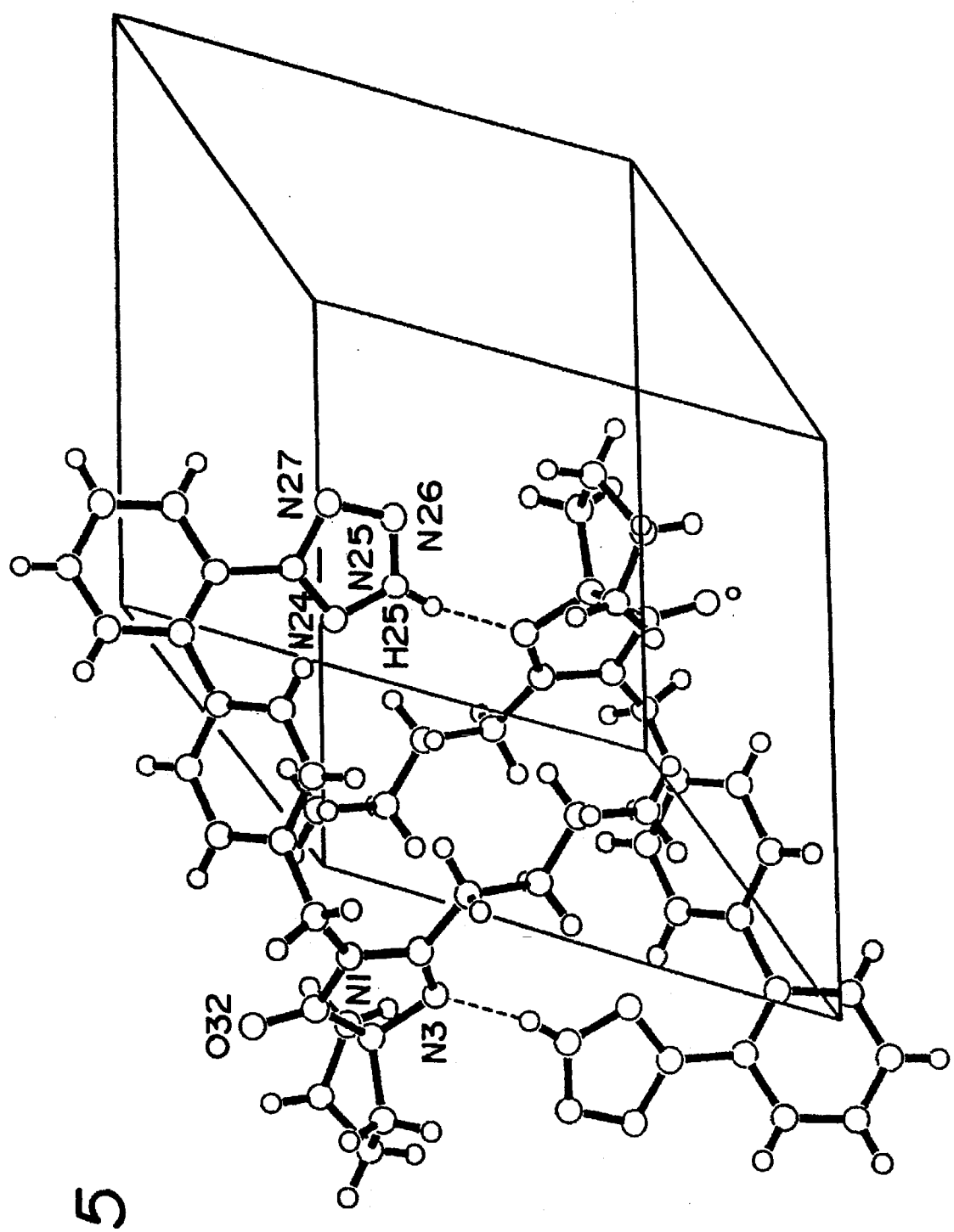

The location of the N(H) hydrogen atom on N(25) is supported by the following facts:
- the H atom next to N(25) was found in the difference Fourier map;
- an N(25)-H. . . N(3)[-x,1-y,-1-z] intermolecular hydrogen bond is present in the crystalline reticle (FIG. 5);
- the N(24)-N(25)-N(26) angle is the largest (114.3°) from the four endocyclic X-N-Y angles while the three other angles are less than 110° (FIG. 4). According to V.S.E.P.R. theory the repulsion of the isolated pair of electrons is stronger than the repulsion in the N-H bond.

Accordingly, the solid state Form B is present in the 2H-1,2,3,4-tetrazole tautomer form.

Until now, attempts to obtain a monocrystal of Form A capable of being analysed at X-rays failed. The microscopic examination indicated that the crystals of the novel Form B are morphologically different from those of Form A.

The Form B of the 2-n.butyl-3-[[2'-(tetrazol-5-yl)biphenyl-4-yl]methyl]-1,3-diazaspiro[4.4]non-1-en-4-one according to the present invention is as active as the known Form A as an angiotensin II receptor antagonist and at least as bioavailable as said Form A. Owing to its low electrostaticity compared to that of Form A, it is particularly useful for the manufacture of pharmaceutical compositions intended for the treatment of all the diseases for which an angiotensin II antagonist is indicated, especially for hypertension.

Thus, according to another of its aspects, the present invention relates to pharmaceutical compositions containing, as the active principle, the Form B of the 2-n.butyl-3-[[2'-(tetrazol-5-yl)biphenyl-4-yl]methyl]-1,3-diazaspiro[4.4]non-1-en-4-one, characterized by the X-ray powder diffraction pattern shown in Table I.

Preferably, the Form B of the 2-n.butyl-3-[[2'-(tetrazol-5-yl)biphenyl-4-yl]methyl]-1,3-diazaspiro[4.4]non-1-en-4-one according to the present invention is formulated in pharmaceutical compositions for oral use containing from 1 to 500 mg of active principle per unit dose, in admixture with a pharmaceutical excipient.

When a solid composition is prepared in the tablet form, the main active ingredient is mixed with a pharmaceutical vehicle such as gelatin, starch, lactose, magnesium stearate, talc, gum arabic or the like. The tablets may be coated with sucrose or other appropriate substances, or else they may be treated so as to present a prolonged or delayed activity and so as to release a predetermined amount of active principle continuously.

A preparation in the gelatin capsules form is obtained by mixing the active ingredient with a diluent and pouring the resulting mixture into soft or hard gelatin capsules.

The water-dispersible granules or powders may contain the active ingredient mixed with dispersants or wetting agents, or suspending agents such as polyvinylpyrrolidone, as well as with sweeteners or taste correctors.

If the active principle is formulated for rectal administration, suppositories are prepared with binders which melt at the rectal temperature, for example cacao butter or polyethylene glycols.

For parenteral administration, aqueous suspensions, saline solutions or sterile and injectable solutions which contain pharmacologically compatible dispersants and/or wetting agents, for example propylene glycol or butylene glycol, are used.

The active principle can also be formulated in the microcapsule form, with one or more carriers or additives if appropriate.

The following examples illustrate the invention without however implying a limitation. The abbreviation THF designates tetrahydrofurane.

EXAMPLE 1

(a) A mixture of 1 kg of 2-n.butyl-3-[(2'-cyanobiphenyl-4-yl]methyl-1,3-diazaspiro[4.4]non-1-en-4-one, 713 g of triethylamine hydrochloride, 337 g of sodium azide in 2 I of 1-methylpyrrolidin-2-one is heated 12 hours under stirring at a temperature of 121°–123° C., then it is left to cool at a temperature of 40°–50° C. A 35% aqueous solution of sodium hydroxide and water are added under stirring thereto and stirring is continued for 30 minutes at a temperature of 20°–40° C. Stirring is stopped, the medium is allowed to settle, the aqueous phase is eliminated and the organic phase is treated with a mixture of water/toluene 5/2. The medium is stirred for 30 minutes at 20°–30° C., then stirring is stopped, the medium is left to settle, the organic phase is eliminated and the aqueous phase is washed by adding ethyl acetate thereto under stirring and the aqueous phase containing the sodium salt of the 2-n.butyl-3-[[2'-(tetrazol-5-yl)biphenyl-4-yl]methyl]-1,3-diazaspiro[4.4]non-1-en-4-one is recovered.

(b) To the resulting aqueous solution of pH 9–11, 36% of hydrochloric acid are slowly added until the pH is 4.7–5.3. At the end of the hydrochloric acid addition, the precipitation of the 2-n.butyl-3-[[2'-(tetrazol-5-yl)biphenyl-4-yl]methyl]-1,3-diazaspiro[4.4]non-1-en-4-one is complete. The resulting suspension is stirred for one hour at 20°–25° C., the product is recovered, wrung at 20°–25° C. and washed with water. A mixture of 500 ml of isopropanol and 4.5 I of water is added to the product thus obtained, the medium is heated one hour at 50°–55° C., then cooled to 20°–25° C. After one hour at this temperature the product is well wrung, the crystals are washed with water and dried at 60° C. In a preparation, 949 g of partially amorphous crude 2-n.butyl-3-[[2'-(tetrazol-5-yl)biphenyl-4-yl]methyl]-1,3-diazaspiro[4.4]non-1-en-4one which are pure at 98%, were obtained (yield: 86%).

(c) 16 I of isopropanol are added to the c, rude product thus obtained and the resulting mixture is refluxed until the product is completely dissolved. The mixture is left to cool at room temperature, then the crystals are filtered off, washed with water and dried. In the same preparation, 901.6 g of the Form A of the 2-n.butyl-3-[[2'-(tetrazol-5-yl)biphenyl-4-yl]methyl]-1,3-diazaspiro[4.4]non-1-en-4-one identical to the product described by C. A. Bernhart et al., J. Med. Chem. 1993, 36, 3371–3380, were obtained. The thus obtained crystals are very electrostatic.

EXAMPLE 2

In another preparation, by operating under the conditions described in Example 1, steps (a) and (b), 970 g of partially amorphous crude 2-n.butyl-3-[[2'-(tetrazol-5-yl)biphenyl-4-yl]methyl]-1,3-diazaspiro[4.4]non-1-en-4-one which are pure at 98% were obtained (yield: 88%).

(c) 7.76 I of 95% ethanol and 1.94 I of water are added to the product thus obtained. The mixture is refluxed, heated 10 minutes and after interruption of heating, seeded with some crystals of Form B. The mixture is left to cool at room temperature under stirring then it is cooled to 15° C. The product is washed with a 1/4 ethanol/water mixture, wrung and dried at 60° C. under reduced pressure. In this preparation, 905.8 g (93.4%) of the Form B of 2-n.butyl-3-[[2'-(tetrazol-5-yl)-biphenyl-4-yl]methyl]-1,3-diazaspiro[4.4]non-1-en-4-one, having a melting point of 185.6° C. and the X-ray powder diffraction pattern given in Table I above, are obtained. The crystals of the Form B are not very electrostatic at all.

EXAMPLE 3

80 ml of 95% ethanol and 20 ml of water are added to 10 g of 2-n.butyl-3-[[2'-(tetrazol-5-yl) biphenyl-4-yl]methyl]-1,3-diazaspiro[4.4]non-1-en-4-one Form A and the mixture thus obtained is refluxed 10 minutes until the solution becomes homogeneous. The mixture is left to cool at room temperature under stirring, then cooled to 15° C. The product is washed with a 1/4 ethanol/water mixture, wrung and dried at 60° C. In this preparation, 8.9 g (89%) of the Form B of the 2-n.butyl-3-[[2'-(tetrazol-5-yl)biphenyl-4-yl]methyl]-1,3-diazaspiro[4.4]non-1-en-4-one, having the same characteristics as those of Example 2, were obtained.

EXAMPLE 4

100 ml of an aqueous solution at pH 2, made acid by hydrochloric acid, are added to 3 g of the Form A of the 2-n.butyl-3-[[2'-(tetrazol-5-yl)biphenyl-4-yl]methyl]-1,3-diazaspiro[4.4]non-1-en-4-one, then the mixture is stirred 24 hours at room temperature (20°–25° C.). The crystals are filtered off and dried at room temperature under reduced pressure. Thus, Form B of the 2-n.butyl-3-[[2'-(tetrazol-5-yl)biphenyl-4-yl]methyl]-1,3-diazaspiro-[4.4]non-1-en-4-one, identical to the product of Example 3, is obtained.

EXAMPLE 5

45 ml of isopropanol are added to 3 g of the Form B of the 2-n.butyl-3-[[2'-(tetrazol-5-yl)biphenyl-4-yl]methyl]-1,3-diazaspiro[4.4]non-1-en-4-one obtained according to Example 3. The mixture is refluxed 10 minutes, left to cool at room temperature under stirring and cooled to 15° C. The product is filtered off, wrung and dried at 60° C. under reduced pressure. Form A of the 2-n.butyl-3-[[2'-(tetrazol-5-yl)biphenyl-4-yl]methyl]-1,3-diazaspiro[4.4]-non-1-en-4-one is thus obtained.

EXAMPLE 6

Starting from the Form A of the 2-n.butyl-3-[[2'-(tetrazol-5-yl)biphenyl-4-yl]methyl]-1,3-diazaspiro[4.4]non-1-en-4-one, operations are carried out exactly as described in Example 5, but, after the 10-minute reflux, the mixture is seeded with some crystals of the Form B and the crystallization operation is continued as set forth in said example. The Form A of the 2-n.butyl-3-[[2'-(tetrazol-5-yl)biphenyl-4-yl]methyl]-1,3-diazaspiro[4.4]-non-1-en-4-one containing traces of the Form B is obtained.

EXAMPLES 7–9

Starting from the Form A of the 2-n.butyl-3-[[2'-(tetrazol-5-yl)biphenyl-4-yl]methyl]-1,3-diazaspiro[4.4]non-1-en-4-one, following the procedure described in Example 3 but varying the 95% ethanol/water ratio, the result given in Table X is obtained.

TABLE X

| Example No. | Ethanol/water v/v | Seeding | Result |
|---|---|---|---|
| 7 | 12/3 | Form B | Form B pure |
| 8 | 5/1 | Form B | Form B pure |
| 9 | 6.3/5 | — | Form B pure |

Note: The volume ratios indicate ml of solvents per g of starting Form A

EXAMPLE 10

30 ml of isopropanol and 15 ml of water are added to 3 g of the Form A of the 2-n.butyl-3-[[2'-(tetrazol-5-yl)biphenyl-4-yl]methyl]-1,3-diazaspiro-[4.4]non-1-en-4-one, and the medium is refluxed 10 minutes, the operations are carried out as described in Example 3. The Form B of the 2-n.butyl-3-[[2'-(tetrazol-5-yl)biphenyl-4-yl]methyl]-1,3-diazaspiro[4.4]-non-1-en-4-one is thus obtained.

EXAMPLES 11–14

Starting from the Form A of the 2-n.butyl-3-[[2'-(tetrazol-5-yl)biphenyl-4-yl]methyl]-1,3-diazaspiro[4.4]non-1-en-4-one following the procedure described in Example 3, but varying the organic solvent and the v/v ratios (ml of solvents per mg of starting Form A), the result given in Table XI is obtained.

TABLE XI

| Example No. | Solvents | v/v | Seeding | Result |
|---|---|---|---|---|
| 11 | THF/water | 11/1.5 | — | Form B pure |
| 12 | methanol/water | 8/2 | Form B | Form B pure |
| 13 | acetone/water | 18/2 | Form B | Form B pure |
| 14 | acetonitrile/water | 8/2 | Form B | Form B pure |

EXAMPLE 15

(a) A solution of hydrochloric acid is added to a solution of 3 g of potassium salt of 2-n.butyl-3-[[2'-(tetrazol-5-yl)biphenyl-4-yl]methyl]-1,3-diazaspiro[4.4]non-1-en-4-one in 30 ml of water until the pH is 4.7. The mixture is stirred, then the thus precipitated crude 2-n.butyl-3-[[2'-(tetrazol-5-yl)biphenyl-4-yl]methyl]-1,3-diazaspiro[4.4]non-1-en-4-one is recovered and dried at 55° C. under reduced pressure.

(b) 24 ml of 95% ethanol and 6 ml of water are added to 1 g of the product thus obtained and the mixture is refluxed 10 minutes. By further operating as described in Example 3, the Form B of the 2-n.butyl-3-[[2'-(tetrazol-5-yl)biphenyl-4-yl]methyl]-1,3-diazaspiro[4.4]non-1-en-4-one is obtained.

EXAMPLE 16

Pharmaceutical composition for oral administration containing the Form B of the 2-n.butyl-3-[[2'-(tetrazol-5-yl)biphenyl-4-yl]methyl]-1,3-diazaspiro-[4.4]non-1-en-4-one as the active ingredient.

| | |
|---|---|
| Active ingredient | 25.0 mg |
| Lactose (Lactose Extra Fine Crystal HMS ®) | 171.0 mg |
| Maize starch (Starch ®) | 50.0 mg |
| Talc | 25.5 mg |
| Colloidal anhydrous silica (Aerosil 200 ®) | 0.5 mg |
| Magnesium stearate | 1.0 mg |

The ingredients are pre-mixed and a previous sifting is carried out, then they are intimately mixed and sifted twice. Capsules of size No. 0, containing 273 mg of the above composition, corresponding to 25 mg of active principle, are finally filled with the mixture thus obtained.

We claim:

1. Process for the preparation of 2-n.butyl-3-[[2'-(tetrazol-5-yl)biphenyl-4-yl]methyl]-1,3-diazaspiro[4.4]non-1-en-4-one which comprises the steps of:

(a) treating 2-n.butyl-3-[(2'-cyanobiphenyl-4-yl)methyl]-1,3-diazaspiro-[4.4]non-1-en-4-one with an alkaline azide and triethylamine hydrochloride in an inert polar aprotic solvent and recovering the resulting 2-n.butyl-3-[[2'-(tetrazol-5-yl)biphenyl-4-yl]methyl]-1,3-diazaspiro[4.4]non-1-en-4-one in the form of one of its alkaline salts in aqueous solution;

(b) neutralizing the alkaline salt of the resulting 2-n.butyl-3-[[2'-(tetrazol-5-yl)biphenyl-4-yl]methyl]-1,3-diazaspiro[4.4]non-1-en-4-one in aqueous medium until the pH is of from 4.7 to 5.3; and (c) crystallizing the product thus precipitated:
either in a solvent containing less than about 10% in volume of water to isolate the 2-n.butyl-3-[[2'-(tetrazol-5-yl)biphenyl-4-yl]methyl]-1,3-diazaspiro[4.4]non-1-en-4-one in its Form A, having the following X-ray powder diffraction pattern:

| d | $I/I_o$ |
|---|---|
| 18.98 | 100.00 |
| 10.89 | 5.81 |
| 9.49 | 7.43 |
| 8.48 | 6.60 |
| 7.13 | 46.23 |
| 6.68 | 11.25 |
| 6.30 | 7.45 |
| 5.45 | 8.85 |
| 5.22 | 16.82 |
| 5.03 | 11.81 |
| 4.71 | 15.91 |
| 4.58 | 45.40 |
| 4.44 | 26.13 |
| 4.32 | 25.44 |
| 4.22 | 25.86 |
| 4.11 | 21.72 |
| 3.93 | 25.46 |
| 3.85 | 33.89 |
| 3.77 | 27.76 |
| 3.38 | 9.09 |
| 3.33 | 11.75 |
| 3.23 | 13.68 |
| 3.14 | 11.99 |
| 2.80 | 8.97 |
| 2.71 | 9.50 | or, in a water-miscible solvent containing more than about 10% in volume of water to isolate the 2-n.butyl-3-[[2'-(tetrazol-5-yl)biphenyl-4-yl]methyl]-1,3-diazaspiro[4.4]non-1-en-4-one in its Form B, having the following X-ray powder diffraction pattern:

| d | I/I₀ |
|---|---|
| 11.22 | 100.00 |
| 7.90 | 12.02 |
| 7.52 | 13.79 |
| 7.23 | 18.60 |
| 6.27 | 20.14 |
| 6.09 | 6.47 |
| 5.86 | 7.42 |
| 5.60 | 98.76 |
| 5.41 | 19.45 |
| 5.05 | 24.67 |
| 4.97 | 20.36 |
| 4.91 | 12.92 |
| 4.80 | 27.33 |
| 4.61 | 15.90 |
| 4.49 | 14.73 |
| 4.36 | 9.86 |
| 4.17 | 62.84 |
| 4.07 | 15.39 |
| 3.97 | 30.34 |
| 3.88 | 14.32 |
| 3.83 | 13.56 |
| 3.75 | 37.28 |
| 3.53 | 26.48 |
| 3.46 | 12.42 |
| 3.40 | 27.88 |
| 3.27 | 11.03 |
| 3.18 | 10.42 |
| 3.15 | 7.28 |
| 3.12 | 6.11 |
| 3.05 | 15.50 |
| 3.01 | 9.49 |
| 2.81 | 7.11 |
| 2.78 | 9.40 |

2. Process according to claim 1, wherein, in step (a), the reaction is carried out with sodium azide in a solvent selected from the group consisting of dimethylformamide and 1-methylpyrrolidin-2-one at a temperature between 110° and 140° C.

3. Process according to claim 1, wherein, in step (c), either isopropanol is used to isolate Form A or an ethanol/water mixture to isolate Form B.

4. Process for the preparation of the Form B of the 2-n.butyl-3-[[2'-(tetrazol-5-yl)biphenyl-4-yl]methyl]-1,3-diazaspiro[4.4]non-1-en-4-one, which comprises recrystallizing the 2-n.butyl-3-[[2'-(tetrazol-5-yl)biphenyl-4-yl]methyl]-1,3-diazaspiro[4.4]non-1-en-4-one in a crude product form or in its Form A from a water-miscible solvent containing at least 10% of water.

5. Form B of the 2-n.butyl-3-[[2'-(tetrazol-5-yl)biphenyl-4-yl]methyl]-1,3-diazaspiro[4.4]non-1-en-4-one obtainable according to the process of claim 1.

6. Form B of the 2-n.butyl-3-[[2'-(tetrazole-5-yl)biphenyl-4-yl]methyl]-1,3-diazaspiro[4.4]non-1-en-4-one obtainable according to the process of claim 2.

7. Form B of the 2-n.butyl-3-[[2'-(tetrazole-5-yl)biphenyl-4-yl]methyl]-1,3-diazaspiro[4.4]non-1-en-4-one obtainable according to the process of claim 3.

8. Form B of the 2-n.butyl-3-[[2'-(tetrazole-5-yl)biphenyl-4-yl]methyl]-1,3-diazaspiro[4.4]non-1-en-4-one obtainable according to the process of claim 4.

9. Form B of the 2-n.butyl-3-[[2'-(tetrazol-5-yl)biphenyl-4-yl]methyl]-1,3diazaspiro[4.4]non-1-en-4-one having the following X-ray powder diffraction pattern:

| d | I/I₀ |
|---|---|
| 11.22 | 100.00 |
| 7.90 | 12.02 |
| 7.52 | 13.79 |
| 7.23 | 18.60 |
| 6.27 | 20.14 |
| 6.09 | 6.47 |
| 5.86 | 7.42 |
| 5.60 | 98.76 |
| 5.41 | 19.45 |
| 5.05 | 24.67 |
| 4.97 | 20.36 |
| 4.91 | 12.92 |
| 4.80 | 27.33 |
| 4.61 | 15.90 |
| 4.49 | 14.73 |
| 4.36 | 9.86 |
| 4.17 | 62.84 |
| 4.07 | 15.39 |
| 3.97 | 30.34 |
| 3.88 | 14.32 |
| 3.83 | 13.56 |
| 3.75 | 37.28 |
| 3.53 | 26.48 |
| 3.46 | 12.42 |
| 3.40 | 27.88 |
| 3.27 | 11.03 |
| 3.18 | 10.42 |
| 3.15 | 7.28 |
| 3.12 | 6.11 |
| 3.05 | 15.50 |
| 3.01 | 9.49 |
| 2.81 | 7.11 |
| 2.78 | 9.40 |

10. Form B of the 2-n.butyl-3-[[2'-(tetrazol-5-yl)biphenyl-4-yl]methyl]-1,3-diazaspiro[4.4]non-1-en-4-one according to claim 9, characterized by having:

a melting point of 185°–186° C.;

IR-characteristic absorbances at 1537, 1200 and 745 $cm^{-1}$.

11. Pharmaceutical composition containing the Form B of the 2-n.butyl-3-[[2'-(tetrazol-5-yl)biphenyl-4-yl]methyl]-1,3-diazaspiro[4.4]non-1-en-4-one, according to claim 9, as the active ingredient.

12. Pharmaceutical composition containing the Form B of the 2-n.butyl-3-[[2'-(tetrazol-5-yl)biphenyl-4-yl]methyl]-1,3-diazaspiro[4.4]non-1-en-4-one, according to claim 10, as the active ingredient.

13. Pharmaceutical composition containing the Form B of the 2-n.butyl-3-[[2'-(tetrazol-5-yl)biphenyl-4-yl]methyl]-1,3-diazaspiro[4.4]non-1-en-4-one, according to claim 5, as the active ingredient.

* * * * *